(12) United States Patent
Levenson et al.

(10) Patent No.: US 9,320,880 B2
(45) Date of Patent: *Apr. 26, 2016

(54) DEVICE FOR FLOW-THROUGH ULTRAVIOLET LIGHT DECONTAMINATION OF MICROBIAL CONTAMINANTS

(71) Applicant: DJLM Innovations, LLC, Pittsburgh, PA (US)

(72) Inventors: David J. Levenson, Pittsburgh, PA (US); John L. Moss, Monroeville, PA (US)

(73) Assignee: DJLM Innovations, LLC, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/934,896

(22) Filed: Jul. 3, 2013

(65) Prior Publication Data

US 2013/0317422 A1 Nov. 28, 2013

Related U.S. Application Data

(63) Continuation-in-part of application No. 12/820,603, filed on Jun. 22, 2010, now Pat. No. 8,496,610.

(60) Provisional application No. 61/269,270, filed on Jun. 23, 2009.

(51) Int. Cl.
*A61M 37/00* (2006.01)
*A61M 39/16* (2006.01)
(Continued)

(52) U.S. Cl.
CPC ............... *A61M 39/16* (2013.01); *A61M 5/142* (2013.01); *A61M 5/172* (2013.01); *A61M 5/5086* (2013.01); *A61M 39/24* (2013.01); *A61L 2/0047* (2013.01); *A61L 2202/21* (2013.01); *A61L 2202/22* (2013.01); *A61M 25/0097* (2013.01);
(Continued)

(58) Field of Classification Search
CPC ............ A61L 2202/21; A61L 2/0047; A61M 2039/167; A61M 2205/12
USPC ................... 604/5.01, 29; 417/477.2; 422/24
See application file for complete search history.

(56) References Cited

U.S. PATENT DOCUMENTS 4,535,247 A   8/1985   Kurtz
4,620,845 A   11/1986  Popovich et al.
(Continued)

FOREIGN PATENT DOCUMENTS

EP   0171834 A2   2/1986
WO   WO-9502324 A1   1/1995
(Continued)

*Primary Examiner* — Emily Schmidt
*Assistant Examiner* — Deanna K Hall
(74) *Attorney, Agent, or Firm* — Fox Rothschild LLP

(57) ABSTRACT

A device for administering a fluid includes a housing that holds a sterilization cassette having a shell, a fluid chamber, and a light transmitting window. An input directs fluid into the chamber. A light source is positioned to direct ultraviolet or other light through the window into the fluid chamber at an intensity sufficient to kill or render non-reproducible at least one species of a microorganism in the fluid while the fluid is in the chamber. An outlet receives fluid from the cassette and directs the fluid to a destination. The fluid is substantially uniformly exposed to the light while in the chamber. The cassette and light source are contained in a housing that prevents light from escaping the housing.

17 Claims, 13 Drawing Sheets

(51) Int. Cl.
   *A61M 39/24*  (2006.01)
   *A61M 5/50*   (2006.01)
   *A61M 5/172*  (2006.01)
   *A61M 5/142*  (2006.01)
   *A61M 25/00*  (2006.01)
   *A61L 2/00*   (2006.01)

(52) U.S. Cl.
   CPC .. *A61M2025/0019* (2013.01); *A61M 2039/167* (2013.01); *A61M 2205/12* (2013.01)

(56) References Cited

U.S. PATENT DOCUMENTS

| | | |
|---|---|---|
| 4,983,307 A | 1/1991 | Nesathurai |
| 5,920,075 A | 7/1999 | Whitehead |
| 5,951,876 A | 9/1999 | Snowball |
| RE36,896 E | 10/2000 | Maarschalkerweerd |
| 6,461,569 B1 | 10/2002 | Boudreaux |
| 6,803,587 B2 | 10/2004 | Gadgil et al. |
| 7,049,615 B1 | 5/2006 | Browne |
| 7,175,760 B2 | 2/2007 | Cary et al. |
| 7,217,933 B2 | 5/2007 | Gadgil et al. |
| 7,270,748 B1 * | 9/2007 | Lieggi ................ 210/198.1 |
| 7,390,417 B2 | 6/2008 | Kuhlmann et al. |
| 7,511,281 B2 | 3/2009 | Cooper |
| 7,566,885 B2 | 7/2009 | Helmore et al. |
| 7,612,492 B2 | 11/2009 | Lestician |
| 7,638,778 B2 | 12/2009 | Chen |
| 7,651,660 B2 | 1/2010 | Kaiser et al. |
| 8,496,610 B2 * | 7/2013 | Levenson et al. ............. 604/29 |
| 2002/0177837 A1 | 11/2002 | Barnitz |
| 2005/0090722 A1 | 4/2005 | Perez |
| 2007/0176117 A1 | 8/2007 | Redmond et al. |
| 2008/0051736 A1 | 2/2008 | Rioux et al. |
| 2008/0159908 A1 | 7/2008 | Redmond |
| 2008/0257355 A1 | 10/2008 | Rao et al. |
| 2008/0306454 A1 | 12/2008 | Sikora |
| 2009/0012450 A1 | 1/2009 | Shah et al. |
| 2009/0012458 A1 | 1/2009 | Childers et al. |
| 2009/0012459 A1 | 1/2009 | Sobue et al. |
| 2009/0134341 A1 | 5/2009 | Chen et al. |
| 2009/0257910 A1 | 10/2009 | Segal |

FOREIGN PATENT DOCUMENTS

| | | |
|---|---|---|
| WO | WO-0247734 A1 | 6/2002 |
| WO | WO-2008084477 A2 | 7/2008 |

* cited by examiner

DEVICE FOR FLOW-THROUGH ULTRAVIOLET LIGHT DECONTAMINATION OF MICROBIAL CONTAMINANTS

RELATED APPLICATIONS AND CLAIM OF PRIORITY

This patent document is a continuation-in-part of, and claims priority to, U.S. patent application Ser. No. 12/820,603 filed Jun. 22, 2010, which claims priority to U.S. Provisional Patent Application No. 61/269,270 filed Jun. 23, 2009. The disclosures of each priority application are incorporated herein by reference in its entirety.

BACKGROUND

This document describes methods and devices that help prevent infections associated with the infusion or ingestion of fluids into the body.

An intravenous catheter is a hollow tube implanted through the skin for temporary or semi-permanent residence in a vein. It is used for infusion of various fluids including blood or blood products, for the withdrawal of blood, or to provide access to the circulation for other diagnostic or therapeutic purposes. Similar catheters may be inserted into arteries or other sterile internal structures for similar purposes. At times any of these catheters may be inserted across other internal body surfaces, including mucosa of the sinuses, oro-pharynx, gastrointestinal tract, genitourinary system, eye conjunctivae, etc. for similar or analogous purposes.

Most often these catheters are inserted into internal regions or structures that are sterile (i.e. devoid of infectious microorganisms). Because these catheters traverse the skin (or analogous body surfaces), they disrupt a crucial barrier preventing the entry of bacteria and other infectious microorganisms from the external environment into sterile regions inside the body. Indeed, such catheters are well known to represent a major source of infections in humans receiving medical care.

Two general mechanisms account for most infections caused by the insertion and continued presence of intravascular catheters, namely:

entry of infectious microorganisms through the skin opening around the exterior of the catheter, permitting them to colonize the catheter's exterior surface, and giving them direct access to subsurface tissues and deeper structures where they may cause infection; and entry of infectious microorganisms, through opening in the fluid circuit connections and junctions, into the interior regions of the fluid circuit, including the lumen of the tubing and the inner surface of the catheter. These microorganisms contaminate the ostensibly sterile fluid, and are carried through the fluid circuit into the sterile interior of the body, causing infection in the blood stream or other structures at the downstream end of the catheter (so-called "intra-luminal infections").

The intravenous fluid circuit is the path of fluid flow from a syringe or fluid bag, through tubing, into the lumen of the intravenous catheter inserted into the body, and then into a blood vessel. This fluid path may include multiple tubing connections and ports. It is imperative that this intraluminal route remain sterile, to avoid introducing infectious pathogens into the circulation.

The catheter is sterilized before use, and routine catheter insertion into the patient utilizes procedures that are designed to maintain sterility. The tubing, ports and connectors upstream of the catheter connection in that fluid infusion circuit, as well as the solutions and medications infused through that circuit ("infusates") are presterilized and connected so as to create and sustain a closed, sterile intraluminal environment throughout the circuit and catheter.

Conventional techniques have been developed to maintain that sterility every time the closed circuit is broken or entered for the infusion of additional fluids or medications, withdrawal of blood, or the attachment of additional circuits, ports, tubing, fluid bags, or devices. Nevertheless, every port and connection in the fluid circuit represents a potential site for the entry of infectious microorganisms.

Whenever a connection in the closed circuit is broken or a sealed port is removed, sterile interior surfaces of the circuit are exposed to the external environment. When so exposed, those sterile interior surfaces may become contaminated with infectious microorganisms, leading to intraluminal contamination and catheter colonization. Despite efforts to prevent these problems, utilizing optimized design of the fluid circuit components, and intensive education and training in preferred methods for sterile accessing of the fluid circuit, intraluminal contamination and infection remain a substantial problem in clinical medicine.

Once the fluid or the sterile internal surfaces of the catheter fluid path become contaminated with infectious microorganisms, it becomes extremely difficult to re-establish a sterile environment. Bacteria can become lodged within the interstices of the non-smooth surface micro-environment of commonly used medical plastics. Furthermore, and most critically, many bacteria secrete a biofilm during growth, which protects and covers the bacteria, rendering them virtually impervious to in situ mechanical, antiseptic and antibiotic eradication measures. In practical terms, once the fluid circuit becomes contaminated, it must be assumed that intraluminal surfaces of the fluid circuit may harbor adherent bacteria that cannot be removed.

Several approaches have been utilized to address actual or suspected catheter infections. The most direct is the removal of the catheter and its associated tubing and fluid bags, with the insertion of a new catheter, typically at another site.

An alternative but less effective method is the removal and replacement of all of the tubing and fluid path components upstream from the catheter, without removal of the catheter itself, in the (often vain) hope that although one or more of the circuit components may be colonized, the catheter itself has been spared.

Yet another approach is to insert a guide wire through the lumen of the catheter into the vein, remove the catheter over the guide wire, and then insert a new catheter over the guide wire into the same vessel location. This approach is sometimes successful. However, it is obvious that the guide wire can collect infectious microorganisms resident on the inner surface of the colonized tubing or catheter, and transfer them to the new catheter, thereby perpetuating rather than eliminating the unwanted colonization.

Antibiotics or antifungal medications have been infused through a contaminated catheter to kill the contaminating microorganisms. This approach has met with limited success most often because of the presence of microbial biofilm on the intraluminal surface of the catheter and other fluid circuit components. In principle, antiseptic solutions might also be used for decontamination of the inner surface of an intravenous catheter, but they are generally not suitable or safe for intravenous infusions at the concentrations needed for this decontamination process.

Another approach is the use of a filter inserted into the fluid path to block the passage of infectious microorganisms downstream of the filter, preventing catheter contamination and intravascular infection. Such filters do not block the passage of all infectious microorganisms, or all of their toxic products, and they do not address any contamination already present downstream of the filter.

U.S. Pat. No. 6,461,569 to Boudreaux discloses a device designed to eradicate infection on the internal surface of an indwelling intravascular catheter. The device utilizes an ultraviolet (UV) light source emitting microbicidal light in the UV-C spectrum. The light source is attached to a fiberoptic bundle that is inserted through the lumen of the intravenous fluid circuit and advanced to the site of presumed infection or bacterial colonization on the inner surface of an intravenous catheter. Irradiation of the bacteria with sufficient intensity and duration of UV light of appropriate wavelength can kill bacteria or render them incapable of proliferation. However, that device does not prevent the initial colonization of the catheter's inner surface, and does not block the infusion of infectious microorganisms into the patient. Furthermore, the use of this device breaks the closed fluid circuit, and therefore creates its own additional risk of microbial contamination of the fluid circuit.

Methods have been described to prevent colonization of the catheter with infectious microorganisms by depositing an antiseptic or antibiotic compound on the surface of the catheter, or within the structure or interstices of the catheter wall. These compounds may diffuse from the catheter wall into the adjacent infusate, blood or body fluid, where they exert their antimicrobial actions. In other arrangements, the compounds are chemically linked to the surface structure of the catheter, and directly interact with the infectious microorganisms in such a manner as to prevent adhesion, proliferation, or survival. Many different specific compounds and salts have been used; examples include silver salts, various antibiotics, and chlorhexidine. Clinical experience suggests that such specially treated catheters have modest but limited efficacy in preventing colonization by infectious microorganisms. The development of biofilm may render these compounds ineffective for their intended purpose.

In addition, problems exist with water supplies, as many supplies are located in remote locations that can become contaminated with microorganisms.

The presence of infectious microorganisms in the luminal fluid is likely to remain an inevitable consequence of the usage of intravascular catheters and similar devices for fluid infusion and blood withdrawal in contemporary medical practice. What is needed, therefore, is a device that will reduce or eliminate the risk that viable infectious microorganisms that may appear in the fluid circuit from being delivered downstream to contaminate the sterile catheter or cause infection of the systemic circulation. It is also desirable to provide a device that reduces or eliminates microorganisms from fluids that will be ingested into the body, such as water spigots or faucets.

SUMMARY

In an embodiment, a device for administering a fluid includes a housing in which a sterilization cassette is seated. The sterilization cassette includes a shell, a fluid chamber, and an light transmitting window. The window may be able to pass one or more types of light, such as visible light or ultraviolet light. An inlet is connected to a first portion of the sterilization cassette and configured to receive a fluid from a source and deliver the fluid to the chamber. A light source, such as an ultraviolet light source or a visible light source, is positioned to direct ultraviolet light through the window into the fluid chamber. An outlet is connected to a second portion of the sterilization cassette so that it may receive the fluid from the cassette and direct the fluid to a destination. The cassette includes channels so that the fluid mixes within the chamber. The light source directs light into the chamber at an intensity sufficient to kill or render non-reproducible at least one species of a microorganism in the fluid while the fluid is in the chamber.

Optionally, the device may also include a tube, such as an intravascular catheter, having a distal tip and a proximal end. The proximal end may be connected to the outlet tube and configured to receive the fluid from the outlet tube and direct the fluid through the distal tip. Alternatively, the inlet tube may include a gasket configured to be attached to a water supply. With either option, a one-way valve may be connected to the outlet tube and positioned to prevent re-entry of the fluid into the outlet tube after the fluid passes through the valve. Either option also may include a flow regulator that limits the flow rate of the fluid into the chamber.

In some embodiments, the light source may include a housing containing, a power supply, a lamp structure that is powered by the power supply, and a positioning structure to seat the cassette in the housing. The housing may be sealed to prevent light from the lamp structure from being emitted outside of the housing when the cassette is seated inside of the housing. A sensor may detect whether the cassette is properly seated in the housing, so that a circuit connected to the sensor that causes the light source to remain off unless the cassette is properly seated in the housing. In addition, a sensor may detect whether the housing is closed to prevent ultraviolet light from escaping the housing, so that a circuit connected to the sensor causes the light source to remain off unless the housing is closed. Also, a sensor may detect whether the light is of at least a predetermined intensity in the chamber, and it may trigger a signal when the light is on but the sensor determines that the light is below the predetermined intensity for a period of time. The signal may be an alarm signal, a signal to keep the light off, or another type of signal. The signal may control a flow regulator that ensures that no fluid flows into the cassette if an alarm condition exists.

Optionally, the light source may emit light at multiple wavelengths in the ultraviolet spectrum. Also optionally, an ultraviolet light-reflective material may be positioned to reflect the light back into the chamber after the light passes from the window through the chamber. Also optionally, one or more interior surfaces of the chamber may be coated with a photocatalytic material that, through oxidation or another process, kills microbes when the coating is exposed to an energy source (such as visible light of sufficient intensity) and contacts the microbes.

Optionally, the housing may include an opening that accepts a downstream end of the outlet tube so that, when inserted through the opening and into the chamber, the downstream end will be exposed to the light.

DETAILED DESCRIPTION

Figure 1:
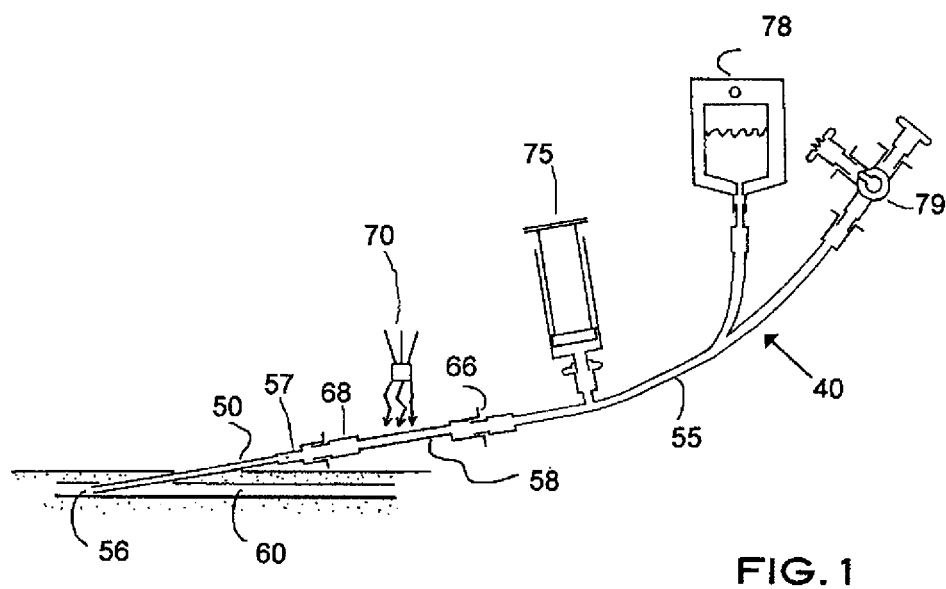
FIG. 1 is an illustration of a simplified fluid circuit for the infusion of fluid into a vein, according to the prior art.

Before the present systems, devices and methods are described, it is to be understood that this disclosure is not limited to the particular systems, devices and methods described, as these may vary. It is also to be understood that the terminology used in the description is for the purpose of describing the particular versions or embodiments only, and is not intended to limit the scope.

It must also be noted that as used herein and in the appended claims, the singular forms "a," "an," and "the" include plural references unless the context clearly dictates otherwise. Unless defined otherwise, all technical and scientific terms used herein have the same meanings as commonly understood by one of ordinary skill in the art. Although any methods, materials, and devices similar or equivalent to those described herein can be used in the practice or testing of embodiments, the preferred methods, materials, and devices are now described. All publications mentioned herein are incorporated by reference. As used herein, the term "comprising" means "including, but not limited to."

Fluid, such as infused through an intravascular (IV) fluid circuit into a vein, is prepared in a sterile fashion and is intended to remain sterile as it flows through the fluid circuit. However, this fluid may be contaminated with microorganisms during preparation or storage, or by the presence of microorganisms that may enter the fluid circuit through various connections or ports. Such organisms may subsequently colonize the fluid circuit tubing, or the IV catheter, leading to continued contamination of the infused fluid and possible infection of the catheter site and the blood stream.

We disclose a device, with its defined components, that prevents or reduces the delivery, into the blood circulation, of viable infectious microorganisms that may be carried in fluid ("infusate") flowing in a fluid infusion circuit such as an IV circuit. The ability to reduce or eliminate the presence of infectious microorganisms in the infusate thereby minimizes or prevents the possibility of microbial colonization of the downstream IV catheter, thereby mitigating or preventing catheter infection, and subsequent systemic infection. In other embodiments, the device may reduce, remove or eliminate microorganisms from ingestible water. In such embodiments, the device may reduce, remove or eliminate microorganisms from ingestible water by killing one or more species of microorganisms or rendering one or more of the species incapable of reproduction.

This device functions by illuminating the fluid, and infectious microorganisms contained therein, as the fluid flows through a specific region of the fluid circuit, with light, such as bactericidal doses of ultraviolet light of wavelength 240-365 nm ("UV-C"). Such light is known to have potent capacity to kill or inactivate a wide range of bacteria, fungi and viruses. One mechanism for this action of UV-C light is the chemical modification of DNA by the production of dimers of pyrimidine nucleotides present in the organisms' DNA, thereby inhibiting DNA replication. Other mechanisms may be used. Without such replication, these microorganisms cannot proliferate and, hence, cannot cause clinical illness. Optionally, light of multiple wavelengths in the UV-C range may be used. Optionally, light in the visible spectrum (e.g., about 390 to about 700 nm) may be used, optionally in combination with a photocatalytic coating on the interior of the device.

FIG. 1 illustrates a conventional IV fluid circuit 40 and a contiguous downstream IV catheter 50 inserted into a region of the body such as a vein 60, according to the prior art. IV fluid enters a delivery tube 55 or 58 from a syringe 75 and/or a fluid reservoir 78. Access into the vein 60 is created by an IV catheter 50 that passes through the skin surface and subcutaneous tissues, and enters the vein 60 with the downstream (distal) tip 56 of the catheter securely within the vein. The upstream (proximal) end 57 of the IV catheter typically has one or more luer lock connections 68 allowing for secure, water-tight and generally bacteriostatic connection to tubing 58 or another device via a complementary luer lock connector. Additional pieces of tubing may be interconnected by additional luer lock connectors 66.

Referring again to FIG. 1, the IV fluid circuit typically includes tubing 55, 58 that is fluidly connected to the upstream end 57 of the IV catheter, through which fluid (sometimes referred to in this document as "infusate") flows, driven by hand pressure, gravity or a pump, from a source such as syringe 75 or fluid reservoir bag 78 into the vein or other internal structure where the downstream end 56 of the IV catheter 50 may reside. Connections between segments or components of the IV fluid circuit and between the IV catheter fluid circuit and the IV catheter are typically accomplished by luer-lock type reversible connections 66, 68, although other methods for connection are also used. Additional sites where the system may be entered include injection ports with open ends, or comprising flexible membranes punctured by needles or other needle-less devices; open-ended segments of tubing; or stopcocks 79 covered by a removable cap or other device. All of these sites represent sites where infectious microorganisms can enter the fluid circuit to contaminate the IV fluid. In the prior art, it has been known to attempt decontamination of fluid in a tube by directing light 70 at the tube. However, this process is not effective and typically cannot be performed in a patient room without exposing the patient to potentially harmful ultraviolet rays.

Figure 2:
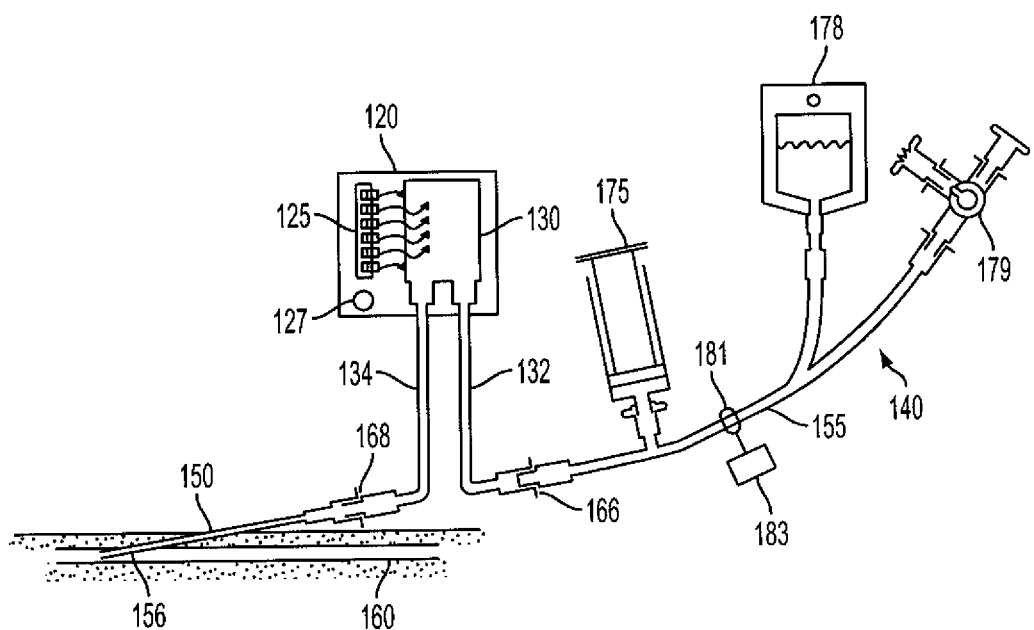
FIG. 2 is an illustration showing examples of elements of a fluid sterilization circuit.

FIG. 2 illustrates an example of a device 140 for administering a fluid with UV or other light-based decontamination. As with FIG. 1, the device 140 in FIG. 2 includes an IV catheter 150 for insertion into a vein, 160. IV fluid enters a delivery channel 155 from an injection cartridge 175, fluid reservoir bag 178 or other source such as one connected via a valve 179 at the end of the tube 155. The distal tip 156 of the catheter may be placed securely within the vein 160.

A sterilization cassette 130 may be positioned to receive fluid from the fluid source via an input tube 132 and direct the fluid to the catheter via an outlet tube 134. The input tube 132 may be connected to the fluid delivery tube 155 via a luer lock connection 166 or other connection device. Similarly, the outlet tube 134 may be connected to the catheter 150 via a luer lock connection or other connection device 168. Thus, fluid from the source may pass through the input tube 132, enter the cassette 130, and then follow the outlet tube 134 to the catheter 150. Optionally, the connection device 168 may include a one-way valve that prevents fluid from re-entering the outlet tube (and thus the cassette) after it passes out from the outlet tube and through the connection device 168. In an alternative embodiment (not shown) the downstream connection 168 is eliminated, and the sterilization cassette's outlet tube 134 and the IV catheter 150 are a single, unified structure, and a one-way valve is substituted for the downstream connection 168. Optionally, the fluid delivery channel 155 may include one or more impellers that form at least part of a fluid turbine 181 that turns as fluid is gravity-fed through the input tube. The fluid turbine may be connected to a generator 183 that generates power in response to the turning of the turbine. The power may be used to power the device.

Optionally, the input tube may be fluidly connected to a flow regulator that ensures that fluid does not enter the cassette at a flow rate that is higher than a predetermined flow rate. The predetermined flow rate will be one that is desirable to ensure that fluid passing through the cassette is exposed to UV light for at least a predetermined minimum exposure time. The cassette 130 may be seated in a housing 120 that also holds an ultraviolet light source 125 that is powered by a power supply 127 (such as a battery or an external wire) and which directs light into the cassette when the cassette is seated in the housing. Irradiation of the fluid in the cassette 130 with sufficient intensity and duration of microbicidal ultraviolet light from the light source 125, at one or more wavelengths in the range of 240-365 nm from the UV light source, will cause elimination, or multi-log reduction in the quantity of viable infectious micro-organisms that may be contained within that fluid. Alternatively, the light source 125 may emit light in the visible spectrum (i.e., about 390 to about 700 nm). In addition, the interior of the light-transmitting window or other interior portion of the cassette may be coated with a photocatalytic material such as titanium dioxide ($TiO_2$). Upon exposure to the light, the photocatalytic material may kill one or more bacteria or other microbes in the fluid through oxidation or another process.

Similarly, if the infusate is known to be sterile, or is made sterile at some alternative sterilization site along fluid path, and if the downstream tubing and the IV catheter are sterile, and if all potential downstream microorganism entry sites are obviated or eliminated (e.g. at the tubing connection to the upstream end of the catheter), then the fluid delivered downstream into the vein or other sterile structure will remain sterile. Furthermore, under such conditions, the inner surfaces of the downstream tubing and IV catheter will remain free of colonization by such infectious microorganisms.

The cassette, housing, and input/outlet tube structure described herein may be detached from the catheter circuit and re-used in other circuits. Alternatively, the cassette, housing, and input/outlet tube structure described herein may be discarded after a single use. Alternatively, instead of being used with a catheter structure as shown in FIG. 2, the cassette 130 and housing 120 may be connected to a fluid source to receive water from an input source such as a valve, spigot, faucet or other delivery mechanism. Water is then passed through the cassette, exposed to UV light and sterilized, and passed through the outlet tube to a spigot or faucet or into a receptacle.

Figure 3:
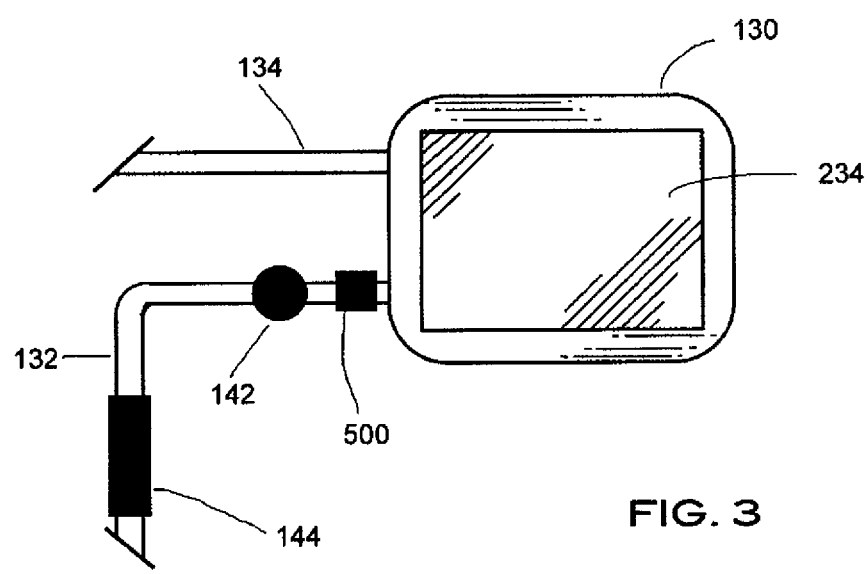
FIG. 3 is an illustration of examples of features of a sterilization cassette.

FIG. 3 illustrates exemplary elements of a cassette 130 that is connected to the input tube 132 and outlet tube 134. One or more surfaces of the sterilization cassette comprises a window 234 capable of transmitting ultraviolet light at one or more wavelengths in the range of 240-365 nm. For example, the window 234 may be made of quartz or another UV-transmissive material. Alternatively or in addition, the window may transmit light in the visible spectrum. Optionally, the inlet tube 132 may be fluidly connected to a flow regulator 142 and/or a filter 144. The flow regulator 142 may be a pinch valve, a flow control valve, a regulator valve, or any other type of flow regulator that limits the flow rate of the fluid entering the cassette so that the rate by which fluid passes through the cassette is controlled, thus ensuring that the fluid is exposed to UV light in the cassette for a desired period of time. Optionally, the flow regulator 142 may be electronically connected to a controller, such as a computer processor or a programmable logic controller, that directs the regulator to increase, decrease, stop, and/or start the flow. In one embodiment, the controller may issue a stop command and/or not permit a start command until the UV light source is on and/or it determines that the housing is closed, the cassette is properly seated, and/or no alarms are triggered. The flow regulator may be controlled by mechanical operation, by an electric signal, or by an electromagnetic field. The flow regulator 142 may include shut-off capability, or a separate shut-off valve 500 may be provided and controlled by the controller. The filter 144 may be a carbon or other filter that filters suspended and/or dissolved solids from the fluid, thus removing particles that may effectively absorb or reflect light if allowed to enter the fluid chamber.

Figure 4:
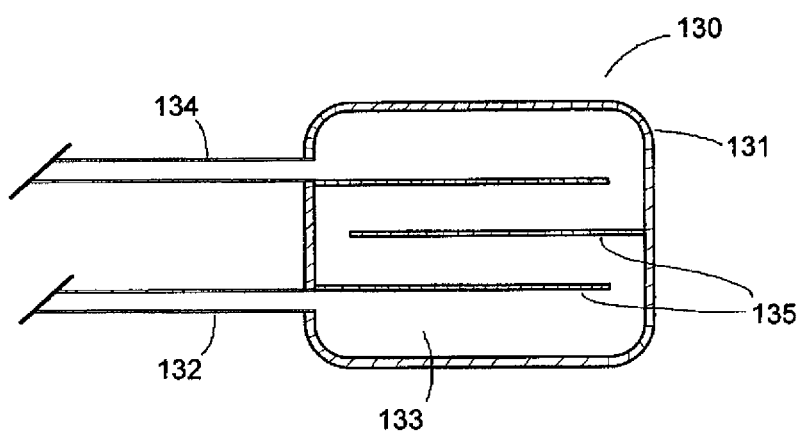
FIG. 4 illustrates additional examples of features of a sterilization cassette.

FIG. 4 shows a cut-away view with the window removed to reveal a fluid chamber 133 that is surrounded by a wall structure (i.e., a shell) 131. Optionally, the chamber may include baffles or other protruding structures 135 that create and/or extend the path for the flow of fluid through the chamber, thus causing turbulence, ensuring that the time in which all fluid passes through the chamber is substantially equal and thus allowing for control of the UV light exposure time for at least some of the fluid that passes through the chamber. The internal fluid path within the fluid chamber 133 may be straight, or it may take one of various routes. These various routes are designed and intended to create turbulence and avoid eddies, thereby ensuring adequate mixing of infusate so that transit time through the sterilization cassette is substantially invariate at any given inflow rate, and exposure to UV light is substantially uniform. For example, the cassette fluid chamber 133 may is provided with walls or baffles 135, positioned perpendicular to the surface of the window 234, that create an internal fluid path with recursive, preformed channels. In another embodiment, the sterilization cassette internal fluid path has recursive, preformed channels or similar arrangements, separated by walls or baffles, said baffles oriented in a plane parallel to the plane of the first surface. In another embodiment the fluid path is split with walls or baffles into a group of parallel channels. In another embodiment the fluid path includes a spiral. In another embodiment the fluid path includes a helix. Various other arrangements, and various combinations and permutations of such arrangements, are possible, and may be used. All such arrangements are included in this disclosure.

Figure 5:
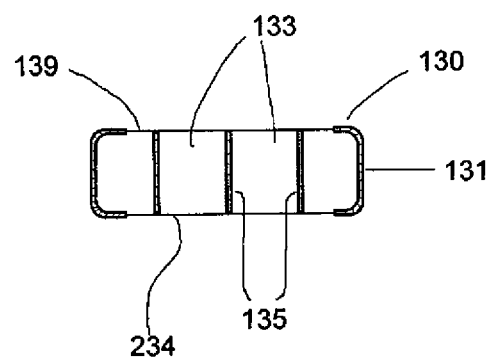
FIG. 5 illustrates additional examples of features of a sterilization cassette.

FIG. 5 is a cut-away side view showing that a second window 139 may be positioned on a side of the chamber that is opposite the first window. The second window may pass light out of the chamber so that it is reflected from a reflecting surface of the interior of the housing and back into the fluid chamber 133. Alternatively, the second window 139 may instead be a reflecting surface that is positioned to reflect light back into the chamber.

Figure 6:
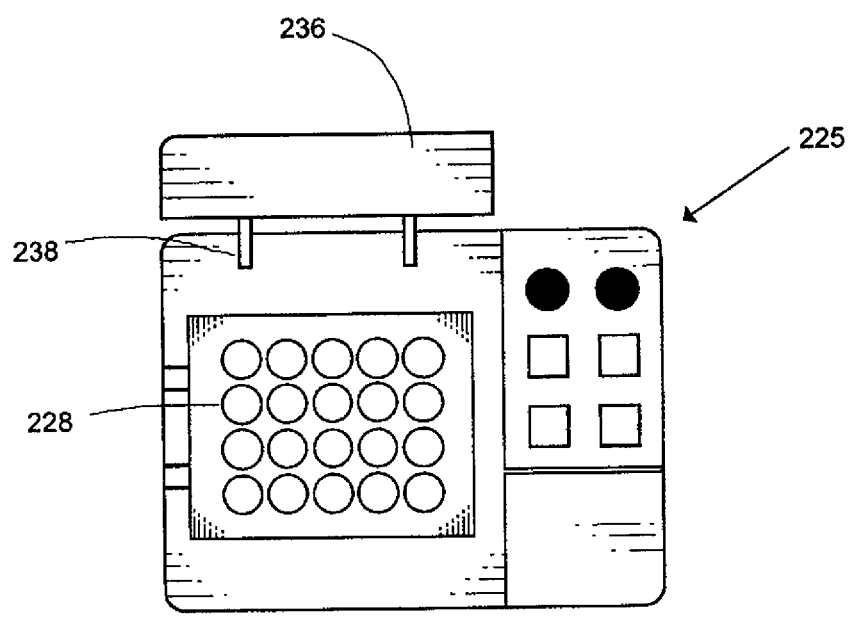
FIG. 6 is a front view of an example of a light source assembly.

FIG. 6 shows an optional light source assembly 225 that includes, among its components, a UV light source 228 that includes an array of light-emitting diodes (LEDs). Overlying the light-emitting surface of some or all of the LEDs may be placed one or more lens or other devices to direct, filter or collimate the emitted light. Each LED or the LED array may include a hermetically sealed housing with lens, heat sink and standard transistor outline header for electrical connections. One embodiment of an LED suitable for this application is an AlGaN/GaN LED with power dissipation of 150 mW, 30 mA current with UV output power of 0.5 mW at 280 nm. An array consisting of two or more such LEDs can be used, depending upon UV output power requirements and other factors. LEDs of different wavelengths can also be combined in the light source. Other lamps and light source structures are possible.

Figure 7:
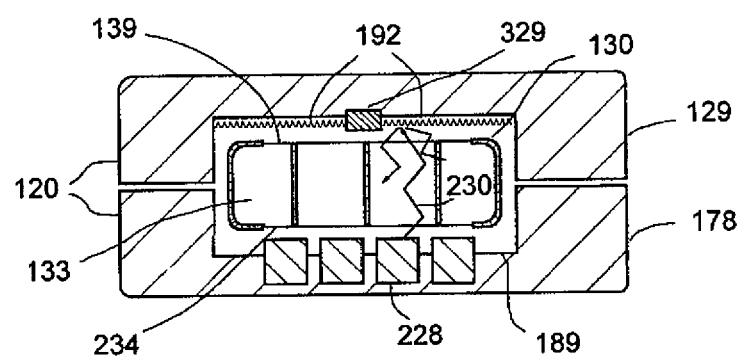
FIG. 7 illustrates a sterilization cassette seated in a housing with a light source.

As shown in FIG. 7, when the sterilization cassette 130 is seated within the housing 120, the transmitting window 234 of the sterilization cassette may be brought in proximity with and aligned to receive light from the light source 228. Light 230, such as UV light that emanates from the light source 228 at one or more wavelengths in the range of 240-365 nm, passes through the window 234 and illuminates fluid flowing in the fluid chamber 133 of the sterilization cassette, causing elimination or multi-log reduction in the quantity of viable infectious micro-organisms in that fluid. Optionally, if the sterilization cassette includes a reflective surface contained on or next to second window 139, or if the cassette includes a second window 139 that is aligned with a reflective surface inside of the housing 120, the light 230 may be reflected back from the reflective surface 192 and into the chamber 133. Various interior surfaces of the housing in the area of the light source may also contain UV-reflective material or other reflective to enhance light delivery to the sterilization cassette.

The inner surface of the housing 120 and the outer surface of the cassette 130 may each contain structures of appropriate shape and design such that the sterilization cassette may be positioned and thus seated securely in its operating position in the housing. For example, the housing may contain one or more depressions or contours, and the cassette may contain corresponding protruding structures or opposing contours, so that the cassette and housing may be properly positioned to have matching or interconnecting contours and thus be seated. The housing and/or cassette may include one or more pressure sensors, positional sensors, or other sensors to detect whether the cassette is properly seated. The sensors may be connected to the circuit to prevent the light source from turning on unless the cassette is properly seated, or to actuate an alarm circuit.

One or more sensors 329 may be positioned on the inner surface of the housing 120 to detect the intensity of light emitted from the light source 228 and transmitted through the sterilization cassette. Other sensors (and their associated visible or UV light sources, if appropriate) may be provided on various surfaces and regions of the light source housing to monitor for variables such as infusate turbidity, satisfactory positioning of the sterilization cassette, complete closure of the light source housing, and other operating parameters.

Thus, FIG. 7 shows that light 230 emanating from the LED array 228 positioned adjacent to the first window 234 passes through the first window 234 to illuminate fluid within the fluid chamber 133. Any light not absorbed or refracted within the fluid chamber 133 passes through the second window 139 and is reflected back from a reflective material 192 positioned on an inner surface of a first piece 129 of the housing 120, again traversing the second window 139 to reenter the fluid path. Any light not absorbed or refracted within the fluid chamber 133 will then pass back through the first window 234, where it may be absorbed, refracted, or reflected by any reflective material it may strike on the inner surface 189 of a second piece 178 of the housing.

Figure 8:
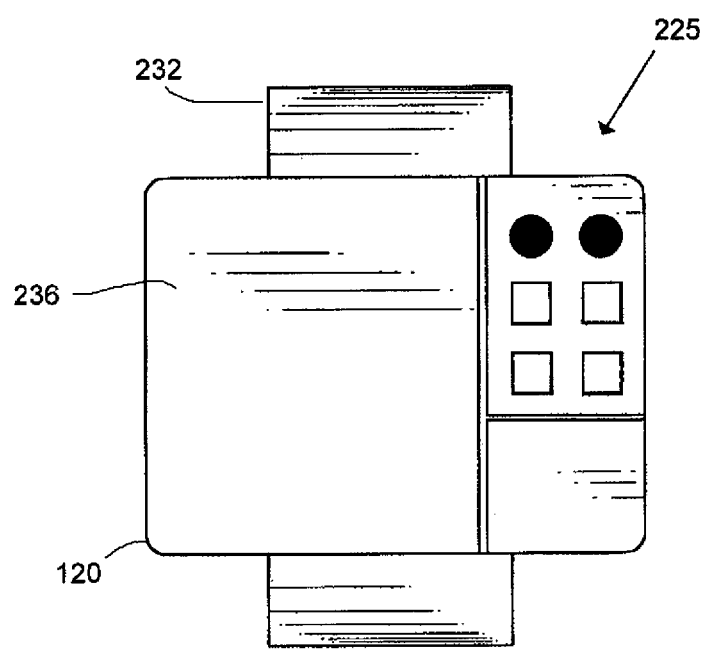
FIG. 8 is a front view of an example of a light source assembly with wearable component.
Figure 9:
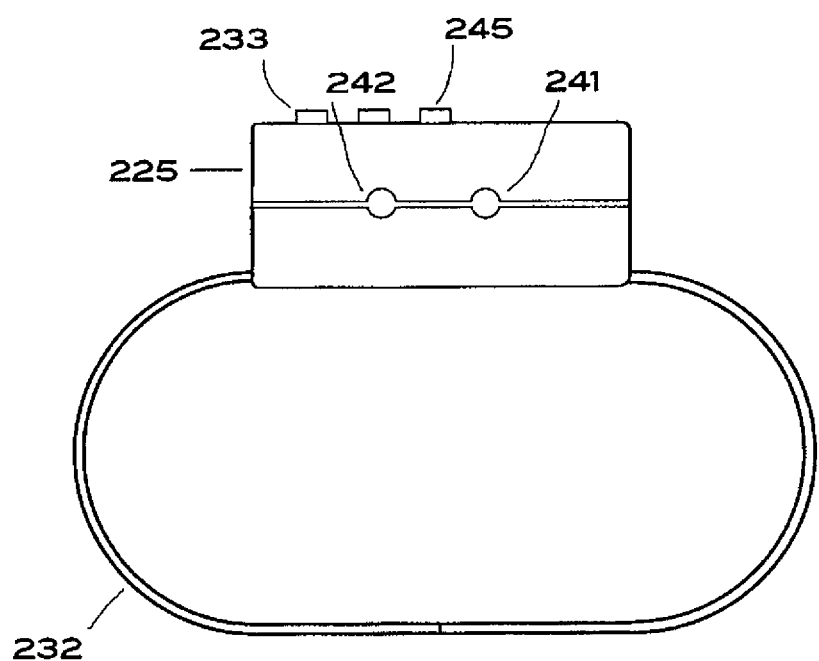
FIG. 9 is a side view of an example of a light source assembly with wearable component.

Referring now to FIG. 8, the light source assembly may include a light source housing 120, and it may optionally include an attachment component 232 for securing light source housing to a limb or other part of a human body in a wearable form. For example, the attachment component 232 may include a wearable armband-like device that may be secured to a limb, with a "one size fits all" design, so as to reduce traction on the IV catheter. In another embodiment, not shown, the attachment component may include a flexible sheet with an adhesive underside for attachment to a body part or surface of the organism or object receiving the infusate, and with a surface mounted holder to secure the light source housing. Optionally, as shown in FIGS. 6 and 8, a cover or lid 236 may be removably or movably secured such as by hinges 238 over the light source when the item is not in use (or when the cassette is in the housing). As shown in FIG. 9, the light source assembly 225 may include openings in its housing 241, 242 through which the inlet tube and outlet tube of the sterilization cassette may pass. Otherwise, the assembly housing may be opaque to UV and/or other light and thus configured to prevent light from passing out of the housing when the UV lamps are powered on. Various surfaces of the housing may be coated, painted or otherwise covered with UV light-absorbing material to prevent escape if UV light from the interior of the light source housing. Flanges may be provided along the surfaces of the first piece and the second piece, to ensure that no path for the emission of light exists between the first piece and the second piece. Internal baffles may be added or substituted and other arrangements provided to prevent external emissions of light from the light source.

FIG. 9 also shows that the housing may include one or more output signal lights or alarms 233, one or more input buttons 245 for control of internal circuitry.

Figure 10:
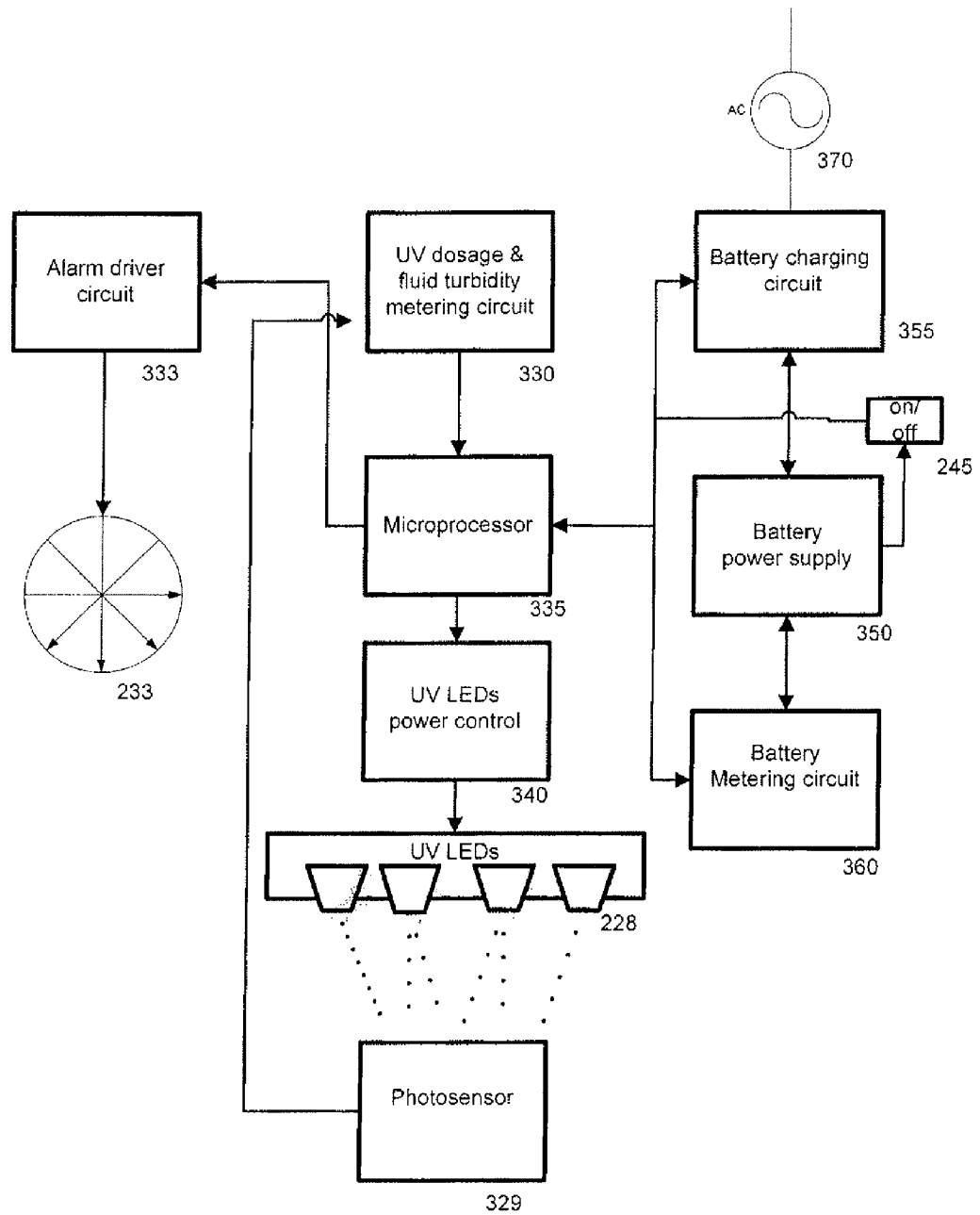
FIG. 10 is a block diagram of an example electronic circuit for a light source assembly.

In various embodiments, the light source assembly 225 may include an internal power supply, connections for external power supplies, monitoring sensors, microprocessor, external input devices, light source, alarm circuits and output devices. FIG. 10 is a schematic representation of an embodiment of the electronic circuitry for the light source assembly. As shown in FIG. 10, the circuit and related structures may include a light source 228 and photosensor 329 that detects when the light source is on.

Optionally, the photosensor 329 may send a signal to a metering circuit 330 and/or microprocessor 335 that ensure that the light is only on if fluid is flowing through the circuit. Other sensors, such as pressure sensors and/or positional sensors, may send signals to ensure that the light is only on if the cassette is properly seated and/or the housing is closed and sealed so that light does not escape the housing. The system may accomplish this by allowing the power control 340 to deliver power to the light source if the fluid is flowing, and optionally only if the cassette is properly seated within the housing. The system also may include an alarm 233 controlled by a driver 333 to indicate whether the device is working properly or not. In addition, an input on-off switch 245 may control connection of the power and/or a battery 350, battery charging circuit 355 and battery metering circuit 360. Optionally, a removable AC power charger 370 also may be provided. The processor also may control an input flow regulator that stops (or does not permit the start of) fluid flow into the cassette if the light is not on, if the housing is not closed and sealed, if the cassette is not properly seated, or if an alarm condition is triggered by any of these or other events.

It may be shown that at any inflow rate, the total transit time through the sterilization cassette is a function of the fluid volume of the sterilization cassette, but not, to a first approximation, related to the route, geometry or length of the fluid path, assuming uniform and complete illumination within the sterilization cassette, turbulent flow and complete mixing of fluid within the sterilization cassette. Hence the fluid volume of the sterilization cassette may be varied to influence the exposure time of fluid within the sterilization cassette to light.

In order to prevent entry of infectious microorganisms into the infusate after exposure of the infusate to UV-C it may be desired that the IV catheter fluid circuit remain impervious to microbial entry at all points downstream from the sterilization cassette. In one embodiment, the sterilization cassette is attached directly to the downstream IV catheter under sterile conditions with a luer lock-type connector that contains a latch mechanism that creates a non-removable connection, impervious to microbial entry, between the downstream connection of the sterilization chamber and the contiguous IV catheter. In such an embodiment, no additional ports, connectors or connection sites are permitted or available downstream from this site. In another embodiment, the downstream connection between the sterilization cassette and IV catheter is sealed, while sterile, with a microbe-impermeable sealant (e.g., cyanoacrylate glue). In another embodiment, the sterilization cassette and the IV catheter are manufactured as a single integral unit.

Figure 11:
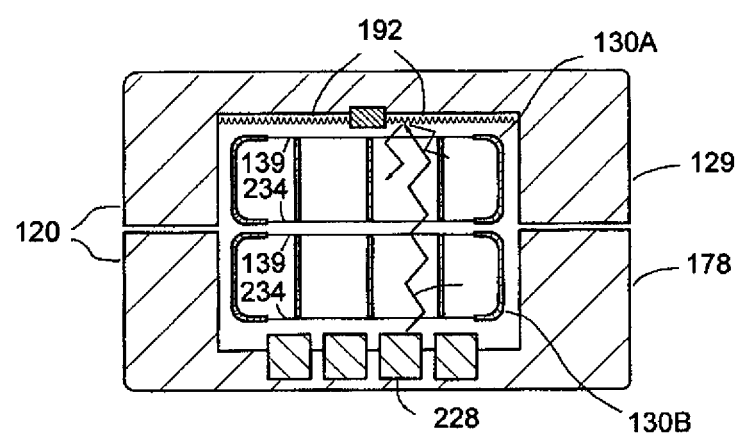
FIG. 11 illustrates two sterilization cassettes seated in a housing with a light source.

The light source described above accommodates a single sterilization cassette. In an alternative embodiment, as shown in FIG. 11, the light source housing 120 may be adapted to accommodate two or more sterilization cassettes 130A, 130B, each containing a first window 234 and a second window 139. The sterilization cassettes may be stacked and oriented atop or alongside one another such that light emanating from the light source 228 that is not absorbed or refracted as it passes through a first sterilization cassette 130B may continue on to illuminate the internal fluid path of a second and any additional sterilization chambers 130A. After exiting the final sterilization chamber 130A in such a stack, the light will then encounter the reflective material 192 on the inner surface of a portion 129 of the light source housing 120. That light will be reflected back through the successive sterilization chambers in reverse order.

Such an arrangement will permit the use of this device for the simultaneous sterilization of infusates flowing into two or more lumens of a multi-lumen IV catheter. In an alternative embodiment, the LED array and the interior space of the sterilization cassette housing may be enlarged so that two or more sterilization cassettes may be accommodated side by side.

Figure 12:
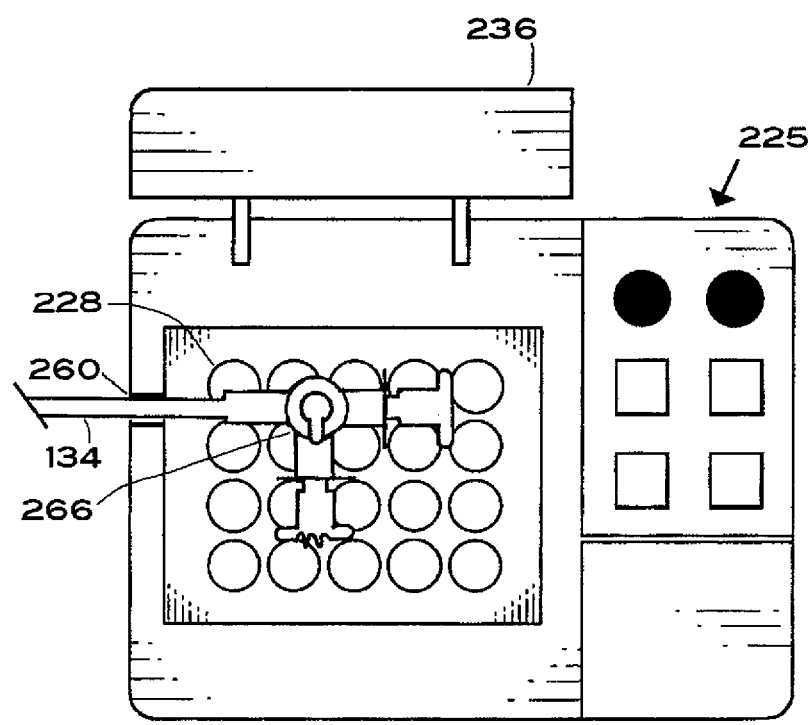
FIG. 12 illustrates a housing configured to receive and sterilize an end structure of a tube.

In an alternate embodiment, exemplary elements of which are shown in FIG. 12, the housing of the light source assembly 225 may include an opening 260 through which the downstream end and associated gaskets 266 or other structures of a sterilization cassette outlet tube or other fluid transmitting tube may be inserted. When the housing's cover 236 is closed and the light 228 is powered on, the end of the tube 134 and end structures 266 may be decontaminated.

Figure 13:
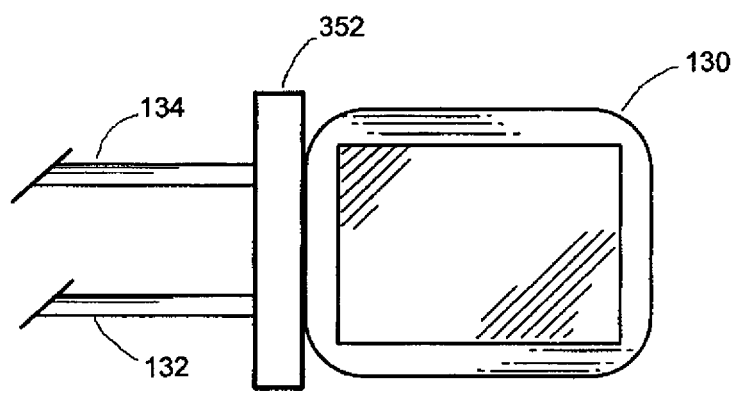
FIG. 13 illustrates example features of an alternate sterilization cassette.

In another embodiment, the first piece 129 and the second piece 178 of the light source housing 120 are manufactured as a single unitary structure, with an opening on one surface of the light source housing, permitting access to an interior space of the light source housing, where the light source is positioned. In this embodiment the sterilization cassette 130 may be modified as shown FIG. 13 to include an opaque panel 352 attached to a side of the sterilization cassette shell, with the attached tubing 134, 132 passing through the panel 352. The panel 352 will be of such shape as to fit and lodge snugly within the aforementioned opening on the surface of the light source housing when the sterilization cassette shell is inserted into the interior space of the light source housing. When the sterilization cassette shell is positioned inside the light source housing such that the panel 352 is snugly lodged within the opening on the surface of the light source housing, the first window and (if provided) the second window of the sterilization cassette will be positioned in the correct orientation and position relative to the LED array and the reflective material.

In another embodiment of this device, the LED or LED array is not provided, and microbicidal light in one or more wavelengths of 240-350 nm is provided by light source consisting of a mercury vapor UV lamp. In one arrangement of this embodiment, the mercury vapor lamp and its associated power supply are not integral with the light source assembly. Rather, light emitted by the mercury vapor lamp may be captured by a UV-transmitting fiber-optic cable, and is delivered by that fiber-optic cable to the sterilization cassette within the interior space of the light source housing where it illuminates the internal fluid path of the sterilization cassette through the first window. The mercury vapor lamp and power supply may be attached to an IV pole or similar support proximate to the light source housing. In an alternative embodiment, the mercury vapor lamp and its associated power supply are miniaturized, and are integral with the wearable light source housing. UV light from the mercury vapor lamp may be delivered to the sterilization cassette by means of mirrors, lenses and/or UV transmitting fiber-optic cable.

This disclosure makes repeated reference to veins, IV catheters, and procedures and infections related to those structures and devices. In analogous applications, a catheter may be inserted into an artery, or any of various other internal sterile body structures or regions for the infusion of fluid or the removal of blood or other internal fluids. It should be understood that when reference is made in this disclosure to the use of this invention for purposes pertaining to veins or IV catheters or infusions, and any related infection issues, that this invention also discloses use of this invention for analogous intra-arterial applications, and for analogous applications where a catheter is inserted through the skin or body surfaces, or body orifice of any organism into another internal sterile structure or region of that organism for the infusion of fluid or the removal of blood or other internal fluids. This disclosure also includes the use of this device and the application of this method for sterilization of flowing or static fluids not infused into biologic systems.

Furthermore, the term "fluid" as used in this disclosure should be understood to include not only water or simple salt or sugar solutions, but also any liquid that may be administered to a human, other animal, plant, or other organism. The liquid may be ingested or otherwise enter into the organism, including natural body fluids, and includes but is not limited to those fluids that may consist of, or contain, medications, proteins, nutrients, blood, blood products, chemotherapy, chemicals, as well as natural body fluids, and any other appropriate compound.

All combinations and permutations of the various embodiments described in this document are included in this invention, as well as other embodiments that may be known or deduced by those skilled in the art or this invention.

By way of example, urine is commonly drained from the urinary bladder into a collecting bag by means of a catheter and its associated tubing. Urine in the collecting bag may become contaminated with infectious organisms; those organisms may be introduced back into the bladder if urine flows retrograde through the tubing into the bladder, such as when the collecting bag is elevated above bladder level. In one embodiment of this invention, the sterilization cassette is connected into the urinary drainage circuit and the connections are sealed, preferably before catheter insertion into the bladder. A flow-limiting valve is included in the urinary circuit to prevent urine flow at a rate beyond the sterilization capacity of the device. In one method of usage of this invention, the sterilization cassette is inserted into the light source housing according to the principles of this invention, and the light source is activated continuously, prior to insertion of catheter into the bladder. By such a process the possibility of bacterial colonization of the urinary bladder by retrograde flow of urine from a contaminated urinary collection bag may be eliminated.

Another embodiment may use devices disclosed herein for sterilizing tap water or other liquids that may be contaminated with infectious organisms. In such an embodiment the attached tubing of the sterilization cassette may include a flow-limiting valve to prevent the fluid flow rate from exceeding the sterilization capacity of the device. The upstream end of the attached tubing may be provided with a gasket such as a screw or clamp connector allowing it to be attached to a faucet or other water supply. The sterilization cassette may be pre-sterilized and hermetically sealed. When ready for use, it may be unwrapped and inserted into the light source housing, which is then switched on. The upstream end of the attached tubing is connected to the water supply and the water supply is turned on. After usage, the sterilization cassette may be discarded to avoid bacterial growth from the downstream tubing.

Various embodiments may be used with indwelling IV catheters, particularly those such as central venous catheters, PICC lines, tunneled central lines, hemodialysis catheters, and the like, that may remain in place for more than a few hours. This device can also be used, if necessary with adaptation by one skilled in the art, with indwelling intra-arterial lines, and other catheters that may be used to deliver sterile fluids into the interior of the body, including into the central nervous system, chest or abdominal cavity, and to deliver sterile fluid to, or adjacent to, peripheral nerves or to similar structures. It is understood that all references to IV catheters in this document also include reference to these other sites of fluid delivery, and all types of catheters and similar devices used for such purposes, whether in humans, other mammals, or in any plant or animal species, or to inanimate objects for similar or analogous purposes.

The sterilization cassette may be provided in a pre-sterilized package. If so, the package may be opened in sterile fashion. The sterilization cassette, along with the IV catheter and the catheter insertion materials and supplies, may be placed in a sterile fashion into the sterile field prepared for IV catheter insertion. In a sterile fashion, the sterilization cassette may be flushed with an appropriate sterile solution from a sterile syringe attached to the upstream port of the sterilization chamber, and the syringe is left in place. The IV catheter may be inserted into the vein under sterile conditions, and then flushed in a sterile fashion with an appropriate sterile solution. The sterilization cassette may then be connected, via irreversible luer lock connector, to the upstream end of the IV catheter. If needed, a sealant, such as cyanoacrylate glue is applied to this connection to create a permanent bacteriostatic seal. The necessary dressings are applied to the site of catheter entry into the skin, and the IV catheter is secured to the skin.

The sterilization cassette is positioned in its operating position within the light source housing and the second piece is closed over it and latched. The light source with its associated electronics is activated, initiating killing of any microorganisms within the sterilization chamber. The syringe is removed from the upstream tubing of the sterilization chamber, and that tubing is connected to the fluid circuit. Infusate flow is initiated, and the light source remains on at all times. The flow rate, exposure time, and light intensity may be selected to kill and/or render the microorganisms incapable of reproduction. Such parameters may be selected or predetermined by testing, depending on the fluid and organisms that will be treated.

Warning lights or other alarms may be activated if battery power falls below preset parameters, allowing the user to replace the battery, or to recharge the battery while the device remains in use. A UV or other light detector may monitor light delivery through the sterilization cassette and initiate appropriate warning signals if the intensity of the received light of a desired wavelength or wavelength range falls below acceptable limits. Such a situation might indicate dirt or debris somewhere in the light path, malposition of the sterilization cassette or failure of the light source. For example, if a fluid solution incompatible with UV-C exposure (e.g., blood, platelets, certain medications), appears in the sterilization chamber, an absorption detection mechanism may immediately identify the condition, disable the UV-C light, and activate a warning signal to notify the user that the UV-C light has been disabled. Detectors may identify if the light source housing is not closed properly, or if other facets of device operation are not within operating ranges, and will activate suitable alarms and necessary safeguards.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the disclosed embodiments.

The invention claimed is:

1. A device for administering a fluid, comprising:
   a housing that contains:
     a sterilization cassette comprising a shell, a fluid chamber comprising a plurality of channels, and an ultraviolet light transmitting window,
     a portion of an input tube connected to a first portion of the sterilization cassette, wherein the input tube is configured to receive a fluid from a source and deliver the fluid to the chamber,
     an ultraviolet light source positioned to direct ultraviolet light through the window into the fluid chamber, and
     a portion of an outlet tube connected to a second portion of the sterilization cassette and configured to receive the fluid from the cassette,
     wherein the channels are configured to create turbulence in the fluid within the chamber, and the ultraviolet light source is configured to provide the ultraviolet light at an intensity sufficient to kill or render non-reproducible at least one species of a microorganism in the fluid while the fluid is within the chamber;
   a channel that delivers fluid from the source to the cassette;
   a turbine comprising one or more impellers positioned within a fluid flow path of the channel;
   a generator that generates electricity in response to actuation of the turbine by fluid moving along the fluid flow path; and
   a tube having a distal tip and a proximal end, wherein the proximal end is connected to the outlet tube and configured to receive the fluid from the outlet tube and direct the fluid through the distal tip.

2. The device of claim 1, further comprising:
   a one-way valve connected to the outlet tube and positioned to prevent re-entry of the fluid into the outlet tube after the fluid passes through the valve.

3. The device of claim 1, further comprising:
a positioning structure configured to property position the cassette in the housing; and
a sensor configured to detect whether the cassette is properly seated in the housing; and
one or more of the following:
- a circuit connected to the sensor, wherein the circuit is configured to prevent the light source from turning on unless the cassette is properly seated within the housing; or
- an alarm circuit configured to actuate if the sensor detects that the cassette is not properly seated in the housing.

4. The device of claim 1, further comprising:
an ultraviolet light-reflective material positioned to reflect the light back into the chamber after the light passes from the window through the chamber.

5. The device of claim 1, further comprising:
a flow regulator;
a controller that controls the flow regulator; and
a sensor configured to detect one or more conditions;
wherein the controller is configured to not permit fluid flow through the flow regulator if the sensor detects an alarm condition.

6. A fluid delivery system, comprising:
a fluid reservoir;
a tube having a distal tip and a proximal end;
a housing that holds:
- a sterilization cassette comprising a shell, a fluid chamber, and a light transmitting window,
- an inlet, wherein the inlet is configured to receive fluid from the reservoir and deliver the fluid to the chamber,
- a light source positioned to direct light through the window into the fluid chamber at an intensity sufficient to kill or render non-reproducible at least one species of a microorganism in the fluid while the fluid is in the chamber, and
- an outlet, wherein the outlet is configured to receive the fluid from the cassette and direct the fluid to the proximal end of the catheter,
- wherein the sterilization cassette is configured so that the fluid mixes within the chamber in a manner so that the fluid is substantially uniformly exposed to the light while in the chamber;
a channel that delivers fluid from the source to the cassette;
a turbine comprising one or more impellers positioned within a fluid flow path of the channel; and
a generator that generates electricity in response to actuation of the turbine by fluid moving along the fluid flow path.

7. The system of claim 6, further comprising:
a one-way valve connected to the outlet tube and positioned to prevent re-entry of the fluid into the outlet tube after the fluid passes through the valve.

8. The system of claim 6, further comprising:
a positioning structure configured to property position the cassette in the housing; and
a sensor configured to detect whether the cassette is properly seated in the housing; and
one or more of the following:
- a circuit connected to the sensor, wherein the circuit is configured to prevent the light source from turning on unless the cassette is properly seated within the housing, or
- an alarm circuit configured to actuate if the sensor detects that the cassette is not properly seated in the housing.

9. The system of claim 6, further comprising:
an ultraviolet light-reflective material positioned to reflect the light back into the chamber after the light passes from the window through the chamber.

10. The system of claim 6, further comprising:
a flow regulator;
a controller that controls the flow regulator; and
a sensor configured to detect one or more conditions;
wherein the controller is configured to not permit fluid flow through the flow regulator if the sensor detects an alarm condition.

11. The system of claim 6, further comprising:
a photocatalytic coating on an interior portion of the cassette.

12. The system of claim 11, wherein the coating comprises titanium dioxide, and the interior portion comprises an interior face of the window.

13. A device for administering a fluid, comprising:
a housing that contains:
- a sterilization cassette comprising a shell, a fluid chamber comprising a plurality of channels, and an ultraviolet light transmitting window, wherein the sterilization cassette is removably seated within the housing;
- an inlet configured to receive a fluid from a source and deliver the fluid to the chamber,
- an ultraviolet light source positioned to direct ultraviolet light through the window into the fluid chamber, and
- an outlet configured to receive the fluid from the cassette and direct the fluid to a destination;
a channel that delivers fluid from the source to the cassette;
a turbine comprising one or more impellers positioned within a fluid flow path of the channel;
a generator that generates electricity in response to actuation of the turbine by fluid moving along the fluid flow path; and
a tube having a distal tip and a proximal end, wherein the proximal end is connected to the outlet and configured to receive the fluid from the outlet and direct the fluid through the distal tip.

14. The device of claim 13, further comprising:
a one-way valve connected to the outlet tube and positioned to prevent re-entry of the fluid into the outlet tube after the fluid passes through the valve.

15. The device of claim 13, further comprising:
a positioning structure configured to property position the cassette in the housing; and
a sensor configured to detect whether the cassette is properly seated in the housing; and
one or more of the following:
- a circuit connected to the sensor, wherein the circuit is configured to prevent the light source from turning on unless the cassette is properly seated within the housing, or
- an alarm circuit configured to actuate if the sensor detects that the cassette is not properly seated in the housing.

16. The device of claim 13, further comprising:
an ultraviolet light-reflective material positioned to reflect the light back into the chamber after the light passes from the window through the chamber.

17. The system of claim 13, further comprising:
a flow regulator;
a controller that controls the flow regulator; and
a sensor configured to detect one or more conditions;

wherein the controller is configured to not permit fluid flow through the flow regulator if the sensor detects an alarm condition.

* * * * *